(12) United States Patent
Rao et al.

(10) Patent No.: US 7,041,986 B2
(45) Date of Patent: May 9, 2006

(54) DEVICE FOR DISCRIMINATION OF FLUORESCENCE LIFETIMES AND USES THEREFOR

(75) Inventors: Govind Rao, Columbia, MD (US); Peter Harms, Ellicott City, MD (US); Iordan V. Kostov, Baltimore, MD (US)

(73) Assignee: University of Maryland Baltimore County, Baltimore, MD (US)

( * ) Notice: Subject to any disclaimer, the term of this patent is extended or adjusted under 35 U.S.C. 154(b) by 387 days.

(21) Appl. No.: 10/389,110

(22) Filed: Mar. 14, 2003

(65) Prior Publication Data

US 2003/0178578 A1 Sep. 25, 2003

Related U.S. Application Data

(60) Provisional application No. 60/364,504, filed on Mar. 14, 2002, now abandoned.

(51) Int. Cl.
*G01N 21/64* (2006.01)

(52) U.S. Cl. .................................. 250/458.1; 250/459.1
(58) Field of Classification Search ............. 250/458.1, 250/459.1, 461.1, 461.2
See application file for complete search history.

(56) References Cited

U.S. PATENT DOCUMENTS

| 5,323,010 | A | * | 6/1994 | Gratton et al. ............ 250/458.1 |
| 5,485,530 | A | * | 1/1996 | Lakowicz et al. .......... 382/191 |
| 5,504,337 | A | * | 4/1996 | Lakowicz et al. ........ 250/461.2 |
| 5,909,278 | A | * | 6/1999 | Deka et al. .................. 356/318 |
| 6,055,451 | A | * | 4/2000 | Bambot et al. .............. 600/476 |
| 6,444,476 | B1 | * | 9/2002 | Morgan ....................... 436/172 |
| 6,741,346 | B1 | * | 5/2004 | Gerstner et al. ............ 356/318 |
| 6,744,503 | B1 | * | 6/2004 | Vo-Dinh et al. ............ 356/318 |
| 6,825,928 | B1 | * | 11/2004 | Liu et al. ..................... 356/317 |
| 2004/0007675 | A1 | * | 1/2004 | Gillispie et al. .......... 250/458.1 |

* cited by examiner

*Primary Examiner*—Albert Gagliardi
(74) *Attorney, Agent, or Firm*—Benjamin Aaron Adler

(57) ABSTRACT

The present invention provides methods for determining fluorescence lifetime of a fluorophor or an optical sensor using frequency domain gated detection. The method comprises the steps of exciting the fluorophor with frequency modulated light from a pulsed light source, gating a photodetector during excitation of the fluorophore, detecting light emitted from the fluorophor with the photodetector, where the emission light exhibits a phase shift in frequency from that of the excitation light, converting the detected excitation light to an amplified electric signal, and evaluating the amplified electric signal as a measure of fluorescence lifetime of the fluorophor. Also provided is a device with which to use the methods disclosed herein.

34 Claims, 13 Drawing Sheets

Gating with square wave excitation

DEVICE FOR DISCRIMINATION OF FLUORESCENCE LIFETIMES AND USES THEREFOR

CROSS-REFERENCE TO RELATED APPLICATION

This non-provisional patent application claims benefit of provisional application U.S. Serial No. 60/364,504, filed Mar. 14, 2002, now abandoned.

BACKGROUND OF THE INVENTION

1. Field of the Invention

The present invention relates generally to the fields of fluorimetry and optical sensors. More specifically, the present invention relates to a filterless device to measure fluorescence lifetime of a fluorophore or of an optical sensor to detect a chemical parameter.

2. Description of the Related Art

Fluorescence sensing is based on excitation of a sensor and measurement of its emission characteristics. This includes fluorescence intensity and fluorescence lifetime. Because excitation and emission occur at different wavelengths, it is possible to resolve them using optical filters. However, any filtering decreases the intensity of the emission which is usually quite low. Additionally, filters are not able to completely exclude the excitation wavelengths. Furthermore, as filters are the most expensive component in an optical system and as it is difficult to integrate filters with electronics and/or chemical sensors, the cost of the device is significantly increased.

Another possibility to discriminate between excitation and emission is to use their time characteristics. If a probe or optical chemical sensor is excited by a light with variable intensity, this results in fluorescence which has well defined characteristics and lags in time. For example, if the probe is excited by narrow pulses of light to create delta-like function pulses, the emission intensity is a series of decay curves. If the detector is turned on a short time after the excitation source is turned off completely, however, the delay, or gate time, prevents scattered excitation light and the emission of short lifetime fluorophores from being detected (FIG. 1). This is referred to as gated detection.

The delta-function-like pulses are achievable using lasers having very short pulse duration and very high peak power. However, the use of lasers in sensing is impractical because of the high cost and volume of the instrument. Laser diodes could be an alternative, however, they are still significantly more expensive than a typical light emitting diode (LED).

Although an LED is almost an ideal excitation source in having a bandwidth up to 100 MHz, a narrow emission spectrum of ~40 nm and efficiency of 5 MW optical power at 40 mA DC, a typical LED does not have sufficient optical power to create delta-function-like pulses. An alternative is to use square wave modulation. The increase of the pulse width increases the signal amplitude. If the period of the excitation is long enough, the starting point of the florescence decay is much closer to the theoretical maximum as determined by the probe quantum yield and concentration. Gating during the excitation pulse from a LED, using a wider gate to accommodate the width increase of the pulse, produces an output signal similar to that using gated impulse excitation from a laser (FIG. 2). However, now the decay curves are separated by a significant time interval equal to half of the period of the excitation light where the output of the photodetector equals zero.

In frequency domain or phase-modulation fluorimetry when the excitation light source is sinusoidally modulated in intensity, intensity of the emission follows the same pattern. That is the emission fluorescence is at the same circular frequency as the excitation light. However, as the fluorophore's excited state is of finite duration, fluorescence lifetime creates a time lag which appears as a phase shift of angle $\phi$ and a decrease in depth of modulation as compared to the circular frequency of the excitation light. A demodulation factor, m, is defined by:

$$m=(B/A)/(b/a)$$

where "A" is the average value of the emitted fluorescence, "a" is the average value of the excitation light, "B" is the amplitude of the peak emission above its average value, and "b" is the amplitude of the peak excitation above its average value (FIG. 3).

The circular frequency of the excitation light is expressed:

$$\omega=2\pi f$$

where f is the excitation frequency in Hertz. The demodulation factor m, which corresponds to the reduction in the depth of modulation compared to that of the excitation, and the phase angle $\phi$ can be measured and used to calculate the modulation lifetime:

$$\tau_m=(\omega^{-1})[(1/m^2)-1]^{1/2}$$

and the phase lifetime:

$$\tau_p=(\omega^{-1})(\tan\phi).$$

The acquired decay curves contain lifetime information for the investigated fluorophore, ambient light and noise. Under strict experimental conditions it is possible to eliminate the ambient light by using a black box and to eliminate the noise through integration. However, in sensors this is hardly possible as the sensing pad is always exposed to some light. Thus phase-modulation fluorimetry methods perform poorly when there is leakage of the excitation or when the lifetimes in a sample significantly differ. The leakage distorts the information rendering it almost useless (FIGS. 4A/4B).

Thus, the inventors have recognized a need in the art for improvement in phase-modulated fluorimetry and in discriminating the lifetime fluorescence of a fluorophore or of an optical sensor of interest in a sample from any background or other fluorophore. The prior art is deficient in as much as the lack of a device that can successfully measure fluorescence lifetime of an optical sensor without using filters. Specifically, the prior art is deficient in the lack of a filterless device for sensing fluorescence lifetimes of a fluorophore using a combination of gated fluorescence detection and phase-modulation fluorimetry. The present invention fulfills these long-standing needs and desires in the art.

SUMMARY OF THE INVENTION

The present invention is directed to a method for determining fluorescence lifetime of a fluorophor comprising the steps of exciting the fluorophor with light from a pulsed light source, gating a photodetector during excitation of the fluorophore, detecting light emitted from the fluorophor with the photodetector, where the emitted light exhibits a phase shift in frequency from that of the excitation light, converting the detected emitted light to an amplified electric signal, and evaluating the amplified electric signal as a measure of fluorescence lifetime of the fluorophor.

The present invention also is directed to a device for determining fluorescence lifetime of a fluorophor comprising a means for delivering a pulsed excitation signal to the fluorophor where the excitation signal exciting the fluorophor to emit a fluorescent signal exhibits a phase shift in frequency from that of the excitation signal, a means for detecting the emission signal emitted from the fluorophor, a means for gating the detection means during delivery of the excitation signal and prior to detection of the emission signal, a means for converting the detected emission signal to an amplified electrical signal; and a means for evaluating the amplified electrical signal as fluorescence lifetime of the fluorophor.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 4A shows a 5 μs lifetime without leakage or scatter. FIG. 4B shows a 5 μs lifetime plus 20% scattered light.

DETAILED DESCRIPTION OF THE INVENTION

Figure 1:
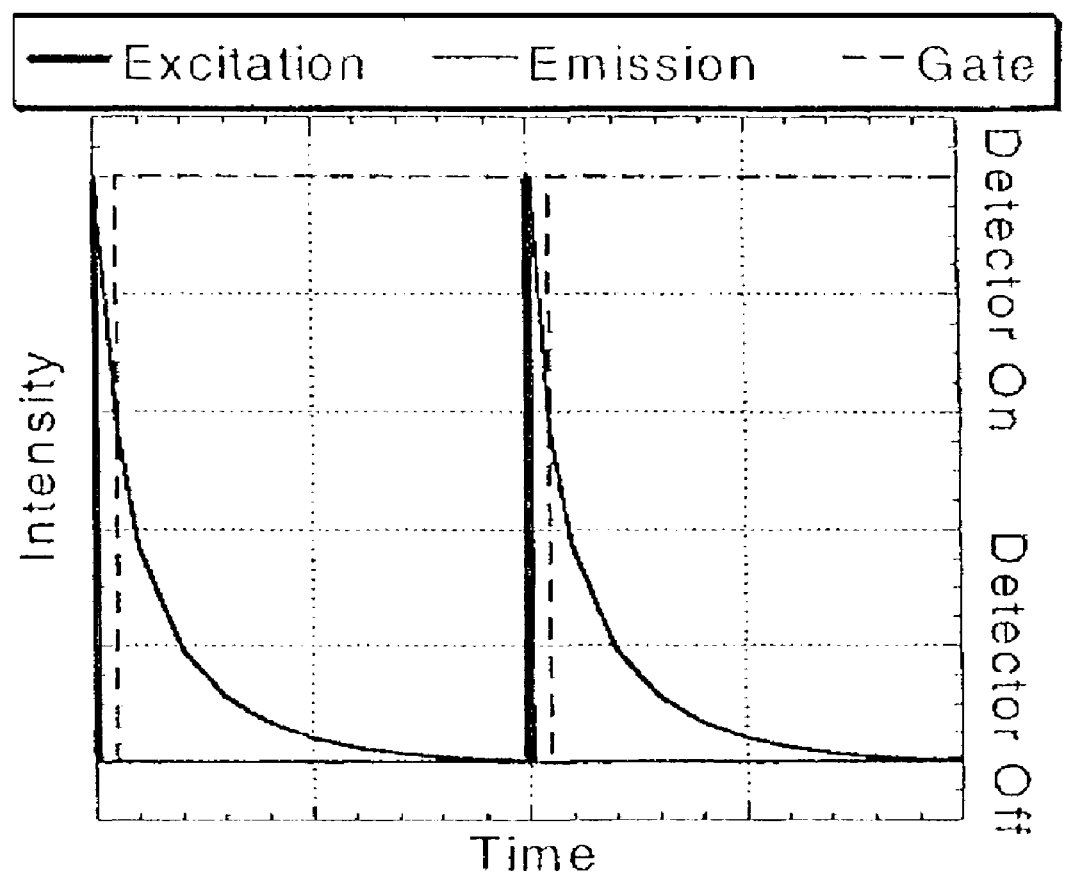
FIG. 1 depicts the separation of a pulsed excitation light and emission light when the signal is gated.
Figure 2:
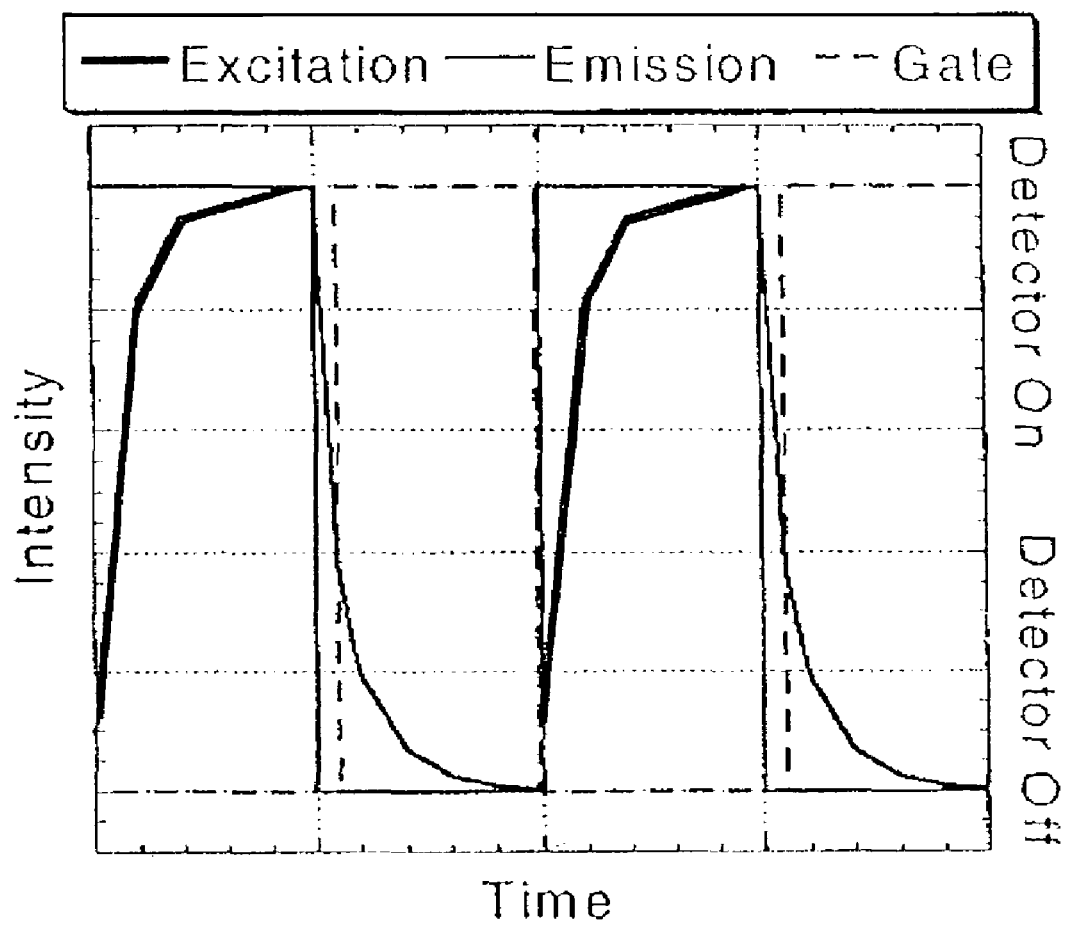
FIG. 2 depicts the separation of LED excitation light and emission light by increasing the pulse width and the gate.
Figure 3:
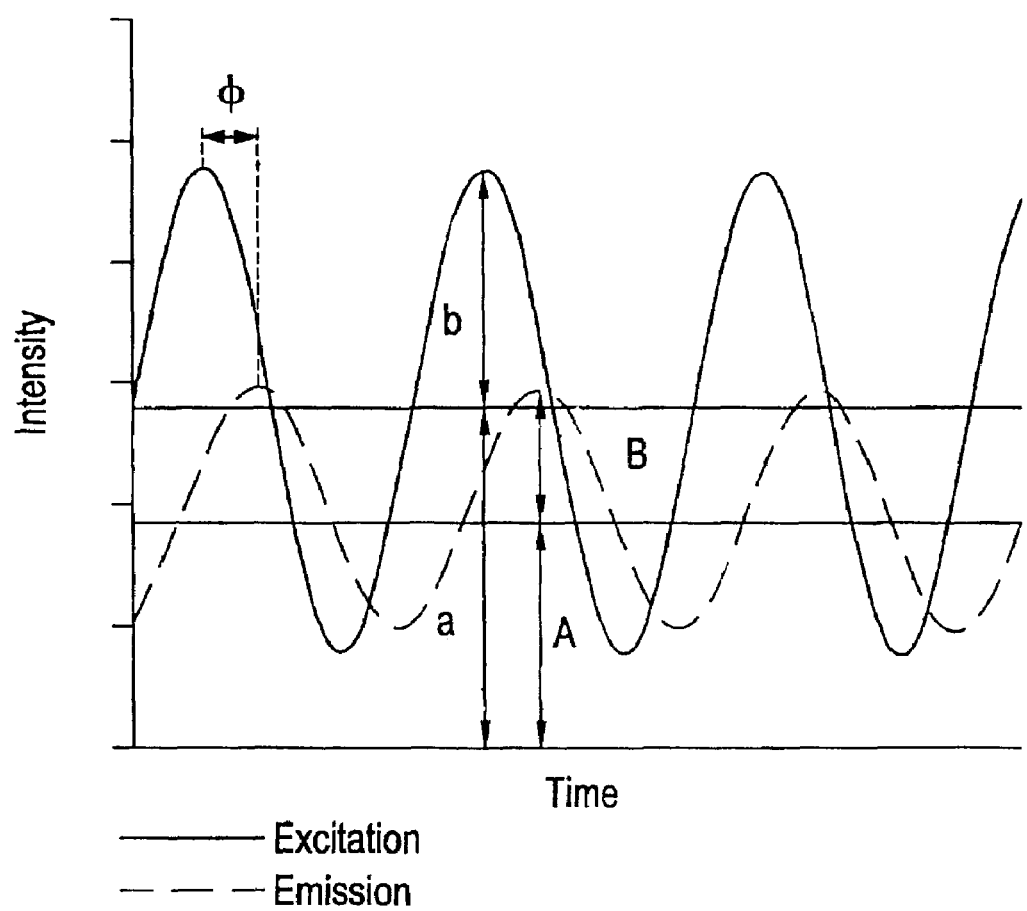
FIG. 3 depicts the relationship between phase shift and depth of modulation in comparing the sinusoidally modulated excitation light with the fluorescence lifetime emission.
Figure 4A:
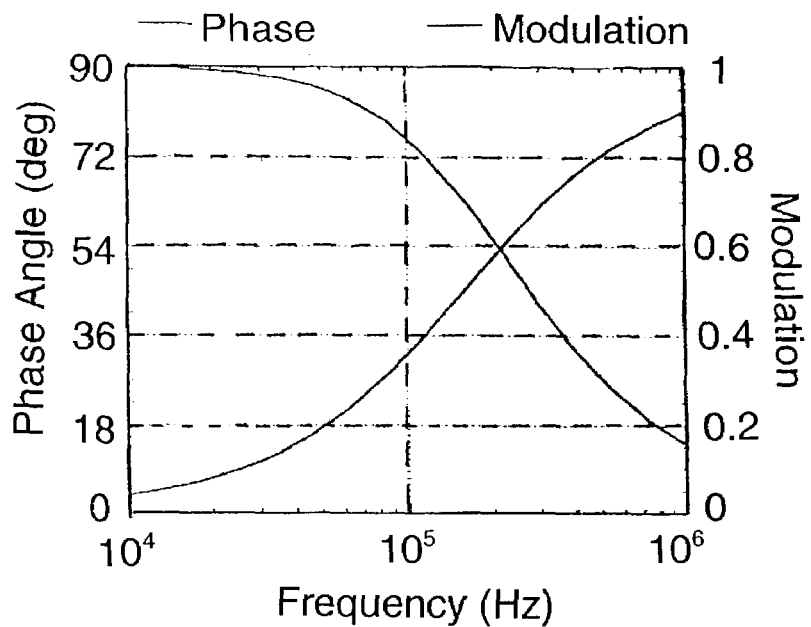
FIGS. 4A and 4B depict the effects of leakage or scatter of the excitation light on the phase angle and modulation of the lifetime emission.
Figure 4B:
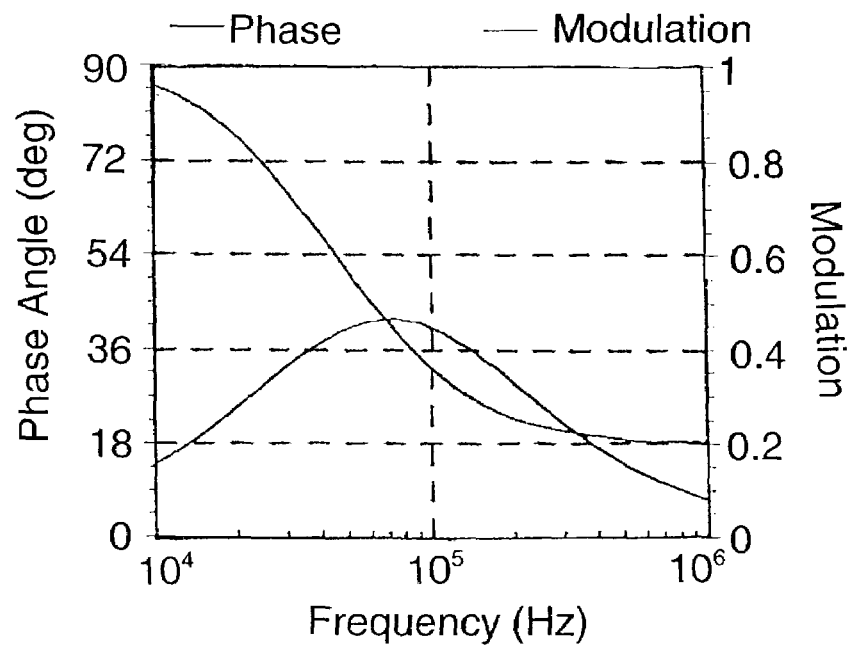

In one embodiment of the present invention there is provided a method for determining fluorescence lifetime of a fluorophor comprising the steps of exciting the fluorophor with light from a pulsed light source, gating a photodetector during excitation of the fluorophore, detecting light emitted from the fluorophor with the photodetector, where the emission light exhibits a phase shift in frequency from that of the excitation light, converting the detected emitted light to an amplified electric signal, and evaluating the amplified electric signal as a measure of fluorescence lifetime of the fluorophor.

In one aspect of this embodiment the pulsed light source is a light emitting diode (LED). The LED may emit light having a wavelength of about 470 nm. The photodetector may be a photodiode.

In another aspect the photodetector is gated with a variable gain amplifier. In a related aspect the photodetector is gated via a first switch and a second switch. In this aspect if one of the first or said second switches is on, the other of the first or said second switches is off. The photodetector is gated when the first gating switch is on and said second gating switch is off. When the second gating switch is on, the photodetector detects the emission signal.

In this aspect gating prevents detection of light other than the measured emission light. Such light may comprise excitation light, ambient light. Additionally, light excluded from detection may be short-lived light comprising scattered light or fluorescence having a time constant about 10 times smaller than the lifetime of the emission light from the fluorophor.

In yet another aspect the emission light is converted to an amplified electric signal via a transimpedance amplifier or a variable gain amplifier. The amplified electric signal is evaluated as fluorescence lifetime via a computer.

In an additional aspect of this embodiment, the method further comprises the step of correlating the fluorescence lifetime of the fluorophor to an analyte present in the immediate environment of the fluorophor or to a parameter of the immediate environment. An example of an analyte is dissolved oxygen or gaseous oxygen.

In all aspects of this embodiment the fluorophor may be used as an optical sensor. An example of an optical sensor is a ruthenium-, a platinum- or a palladium-based ligand complex. Specific examples of the complex are tris(4,7-diphenyl-1,10-penanthroline) ruthenium (II) salt or tris-2,2'-bipyridyl ruthenium (II) salt.

In another embodiment of the present invention there is provided a device for determining fluorescence lifetime of a fluorophor comprising a means for delivering a pulsed excitation signal to the fluorophor where the excitation signal exciting the fluorophor to emit a fluorescent signal exhibits a phase shift in frequency from that of excitation signal, a means for detecting the emission signal emitted from the fluorophor, a means for gating the detection means during delivery of the excitation signal and prior to detection of the emission signal, a means for converting the detected emission signal to an amplified electrical signal; and a means for evaluating the amplified electrical signal as fluorescence lifetime of the fluorophor. In all aspects of this embodiment the light source, including an LED, the photodetector, the optical sensors, the analytes and the fluorophores are as described for the method presented herein.

In one aspect of this embodiment, the means for delivering the excitation signal comprises a light emitting diode (LED) and a driver thereof. The LED may emit an excitation signal having a wavelength of about 470 nm. Also in this aspect the means of detecting the emission light is a photodiode.

In another aspect the means for gating the photodetector is a variable gain amplifier. In a related aspect the means for gating comprises a first and a second switch. In this aspect the switches function as described supra. A further aspect has a means of converting the detected emission signal to an amplified electrical signal using a transimpedance amplifier or a variable gain amplifier.

In yet another aspect the means for evaluating the amplified electric signal comprises a computer which has means to receive the amplified electric signal. The computer further comprises means for synchronizing interaction of all of the means used in the device. In this aspect the computer synchronizes interaction of all of the means comprising the device via an analog-to-digital converter/data conversion card (ADC/DAC). In yet a further aspect the computer comprises means for correlating the fluorescence lifetime of the fluorophor to an analyte present in the immediate environment of the fluorophor or to a parameter of said immediate environment as described supra.

The following terms shall be interpreted according to the definitions set forth below. Terms not defined infra shall be interpreted according to the ordinary and standard usage in the art.

As used herein, "frequency domain fluorimetry or phase-modulation fluorimetry" shall refer to measurements of fluorescence lifetimes using modulated light source, sine wave modulated detector, and detection of the phase shift between the excitation and emission light.

As used herein, "gated fluorescence detection" shall refer to fluorescence detection in which the photodetector is turned on after the excitation source is turned off.

As used herein, "frequency domain gated detection" shall refer to frequency domain fluorimetry in which pulsed light sourse is used and the photodetector is turned on after the excitation source is turned off.

The present invention provides methods and a device that combines gated fluorescence detection and phase-modulation fluorimetry thus precluding the need to use filters to resolve excitation and emission wavelengths. The methods and device of the present invention can successfully measure the fluorescence lifetime of a fluorophor without wavelength separation even in the presence of ambient light and/or strong autofluorescence. Additionally, the device uses an inexpensive excitation light source and emission photodetector thereby significantly lowering the cost of the hardware in the device.

Phase modulation fluorimetry using a gated signal provides a method of discriminating the fluorescence lifetime decay of a fluorophore of interest from that of, inter alia, ambient light and scattered excitation which exists for several picoseconds. light and emission from other short lifetime fluorophores. Gating further excludes any short-lived fluorescence that has a time constant about 10 times smaller than the lifetime of the measured signal. The excitation and the ambient light are not detected because a photodetector used to detect emitted light from the fluorophore is gated.

Figure 5A:
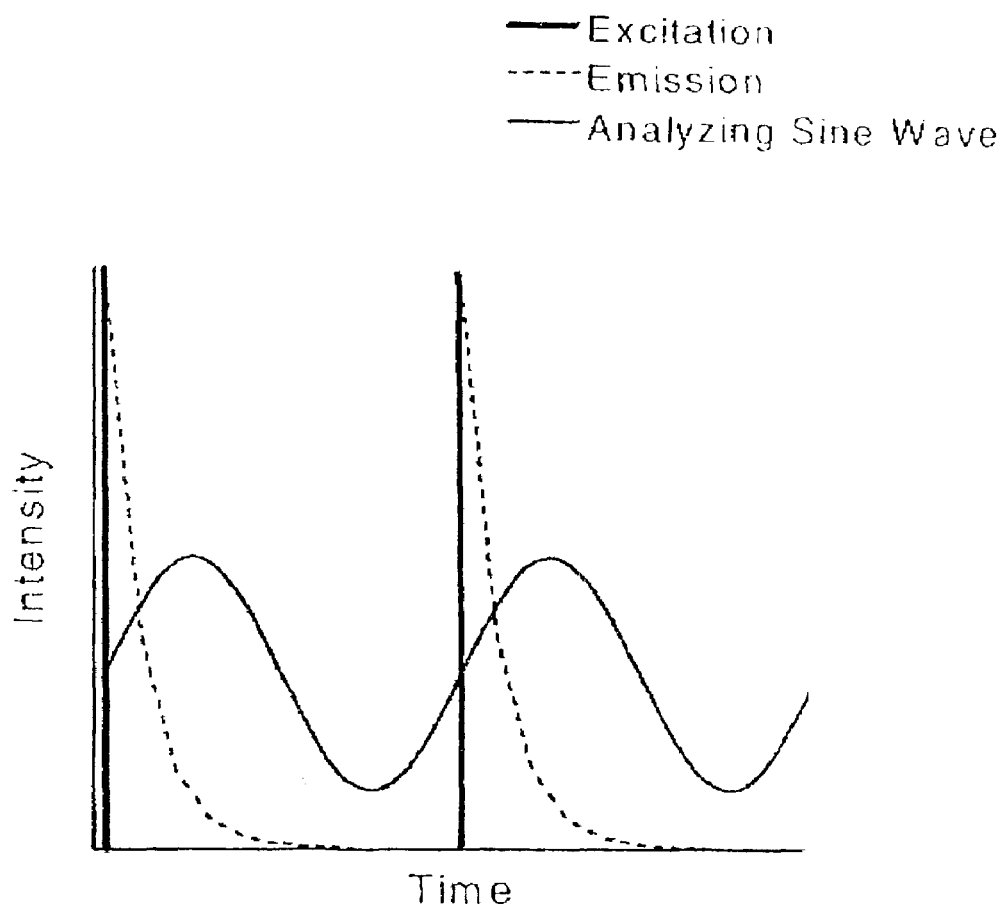
FIG. 5A demonstrates that multiplying a pulsed excitation signal by a sinusoidal function of the same frequency, both in-phase and quadrature, and integrating the result eliminates the effects of ambient light.
Figure 5B:
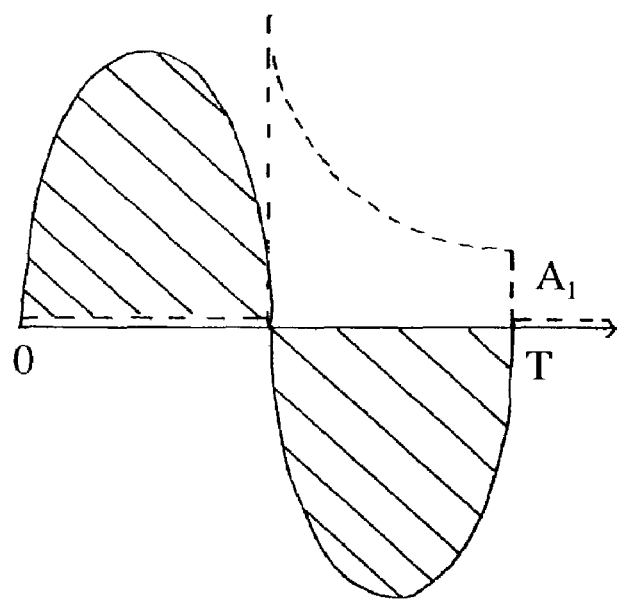
FIG. 5B demonstrates that multiplying a square wave excitation signal by a sinusoidal function of the same frequency and integrating the result does not eliminate the effects of ambient light.

One approach to eliminate the effects of ambient light is to multiply the signal by a periodic function and to integrate the result. In Frequency Domain Gated Detection, the signal is multiplied by a sinusoidal function of the same frequency, both in-phase and quadrature, and integrated. The ratio of the integrals is proportional to tan ϕ, where, as demonstrated supra, tan ϕ=ωτ, ω=2 πf, f is the excitation frequency and τ is the fluorophor lifetime. This detection method is successfully applied to impulse excitation (FIG. 5A). However, if the signal from the square wave excitation is multiplied and integrated, the ambient light ($A_1$) is included in the result which greatly alters the measurement as demonstrated below (FIG. 5B).

By defining the parameters as:

$$A(x) = \sin 2\pi/T$$

and $$B(x) = \begin{vmatrix} 0, T/2 > x > 0 \\ A_0 \exp(-x/\tau) + A_1 \end{vmatrix}$$

then the integral of the product of A(x) and B(x) is defined as:

$$\int_0^T A(x) \cdot B(x)\, dx = A_0 F(\exp(-x/\tau), \sin(2\pi/T)) + 2\pi A_1$$

Figure 5C:
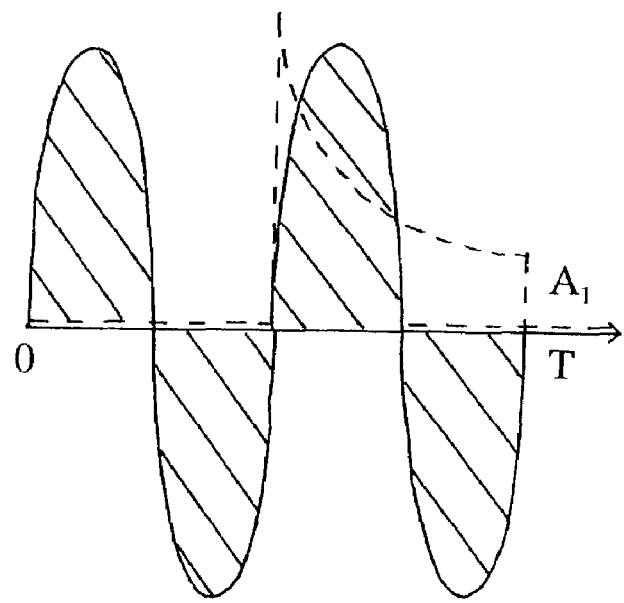
FIG. 5C demonstrates that multiplying a square wave excitation signal by double the frequency of the sinusoidal function and integrating the result does eliminate the effects of ambient light.

The solution is to multiply the signal by the doubled frequency of the excitation light (FIG. 5C). By defining the parameters as:

$$A(x) = \sin 4\pi/T$$

and $$B(x) = \begin{vmatrix} 0, T/2 > x > 0 \\ A_0 \exp(-x/\tau) + A_1 \end{vmatrix}$$

then the integral of the product of A(x) and B(x) is:

$$\int_0^T A(x) \cdot B(x)\, dx = A_0 F(\exp(-x/\tau), \sin(4\pi/T))$$

and ambient light ($A_1$) is not factored into the integral.

If the signal is multiplied by a sinusoid, the output will be proportional to tan ϕ and the influence of the ambient light is eliminated and the solution of the integrals is:

$$U(x) = \int_0^T \operatorname{Sin}((4\pi/T)(x)) \cdot B(x)\, dx = A_0 \tau (1 - \exp(-x/\tau))\operatorname{Cos}(\varphi)$$

and $$V(x) = \int_0^T \operatorname{Cos}((4\pi/T)(x)) \cdot B(x)\, dx = A_0 \tau (1 - \exp(-x/\tau))\operatorname{Sin}(\varphi)$$

where the resulting ratio is : V(x)/U(x)=tan(ϕ).

Figure 5D:
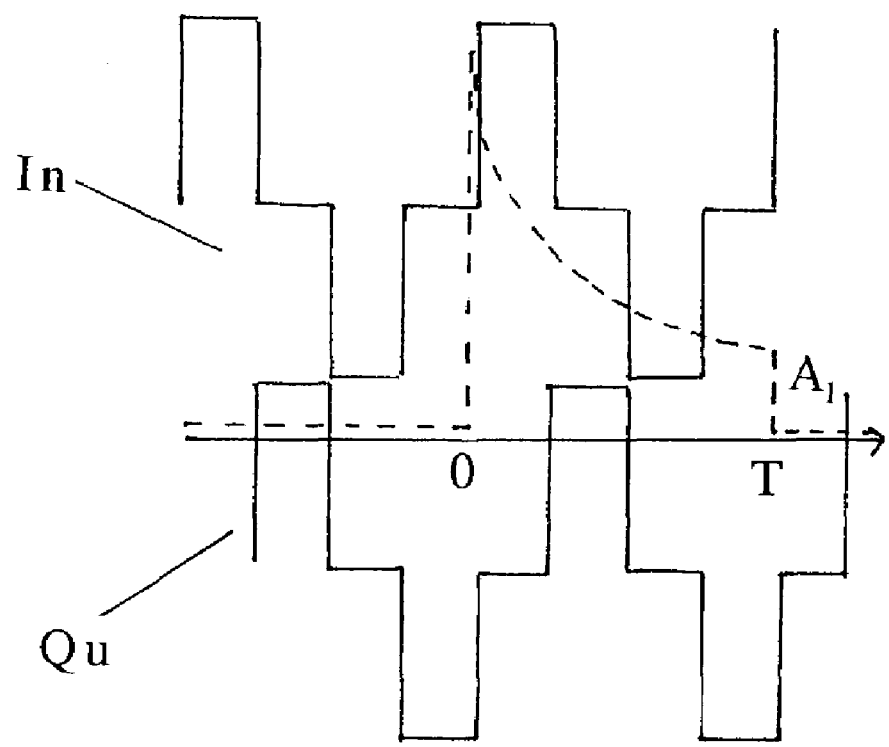
FIG. 5D demonstrates that multiplying a square wave excitation signal by a sinusoidal function of the same frequency, both in-phase and quadrature, and integrating the result eliminates the effects of ambient light.

Furthermore, a square wave signal, in-phase (In) and quadrature (Qu) can be used for mixing (FIG. 5D) where the resulting signal is proportional to $\exp(-\pi/2\omega\tau)$. The parameters are defined as:

$$In(x) = \begin{cases} 1, & 0 < x < T/4 \\ 0, & T/4 < x < T/2 \text{ and } 3T/4 < x < T \\ -1, & T/2 < x < 3T/4 \end{cases}$$

$$Qu(x) = \begin{cases} 0, & 0 < x < T/4 \text{ and } T/2 < x < 3T/4 \\ 1, & T/4 < x < T/2 \\ -1, & 3T/4 < x < T \end{cases}$$

$$B(x) = A_0 \exp(-x/\tau) + A_1$$

In this case, $$V(x) = \int_0^T B(x) \cdot In(x) \, dx$$

and $$U(x) = \int_0^T B(x) \cdot Qu(x) \, dx$$

where the resulting ratio is: $V(x)/U(x) = \text{Exp}(-T/4\tau)$. The choice of the form of the mixing signal depends on the desired accuracy and sensitivity of the device as well as on its hardware realization.

The device of the present invention may use external gating switches. Possible schemes using external gating include placing switches between the photodetector and the transimpedance amplifier, placing switches after the transimpedance amplifier and placing switches in the feedback of the transimpedance amplifier thus modulating it amplification. In any of these schemes when one of the switches is on, the other is always off.

The device also uses readily obtainable and inexpensive solid state optoelectronics for an excitation light source and emission photodetector. An LED and a PIN photodiode provide almost ideal excitation source and photodetector, respectively, each device costing a few dollars or less.

Table 1 provides the characteristics of a representative LED and PIN photodiode. Additionally, the device uses a computer as a controller with appropriate input/output features, such as an analog-to-digital converter/data acquisition card (ADC/DAC). Furthermore, the computer may comprise software to perform any needed mathematical functions.

TABLE 1

| | Component | |
|---|---|---|
| | LED | PIN photodiode |
| Speed | | |
| Bandwidth | up to 100 MHz | 40 MHz–100 GHz |
| Emission spectrum | approx. 40 nm | |
| Efficiency | | |
| Optical power | 5 mW @ 40 mA DC | |
| Quantum yield | | greater than 0.9 |

In a preferred embodiment the excitation source is a high-brightness, blue LED MBB515AH-T (Microelectronics Corp., Santa Clara, Calif.) with maximum wavelength 470 nm, 40 nm FWHM, luminous intensity 4000 mcd. The LED is driven using custom-built voltage controlled current sources with shutdown. It is operated in pulsed mode using a rectangular square wave with 50% duty ratio at a peak current of 100 mA. The total output optical power from the blue LED is approximately 4 mW. The LED current is modulated at frequency $f_{mod}$=35 kHz. The fluorescence is collected using a large active area, i.e., 13 mm$^2$ PIN photodiode S1223-01 (Hamamatsu, Bridgewater, N.J.). The LED and the photodiode are mounted as close as possible to the cuvette with the sample.

Figure 6:
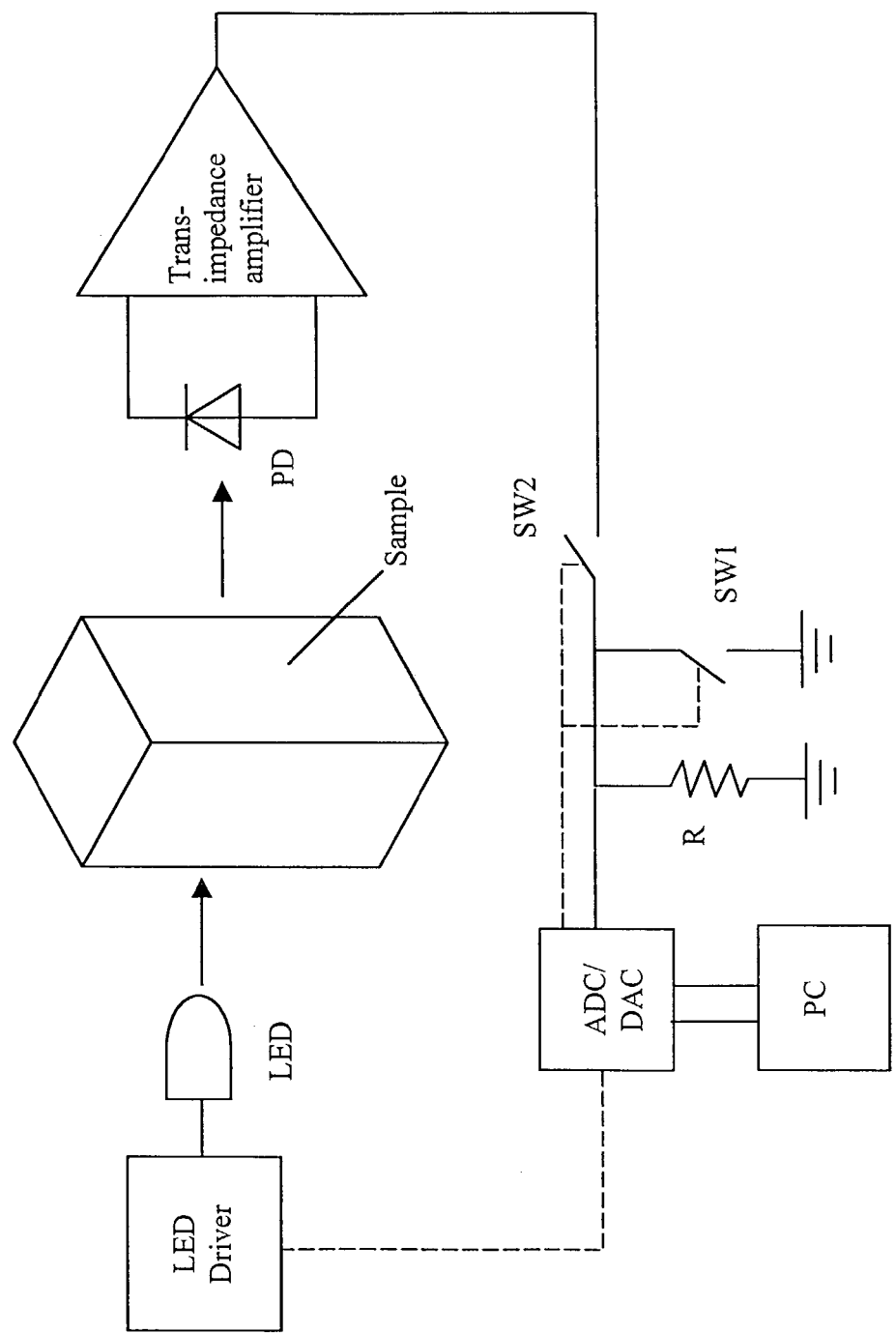
FIG. 6 depicts a block diagram of the filterless device.

FIG. 6 depicts the block diagram of the electronics. The modulation frequency is controlled by a computer via the digital outputs of the ADC/DAC. The gating semiconductor switches (CD4060) are driven by the same outputs. The LED driver is synchronized with the gate. A high-speed switch gates the output signal. When the LED is on, switch SW1 is on and switch SW2 is off. When the LED is off, switch SW1 is off and switch SW2 is on. The detected fluorescence is converted into an electrical signal by a fast, e.g., 3 MHz bandwidth, transimpedance amplifier and is fed via the switches to the load resistor and ADC. All further mathematical operations such as background correction, sine and cosine transforms, and the determination of the phase and modulation are performed in Labview 5.1. It is contemplated that a low-cost portable device for sensing applications is realized.

The fluorophores of the present invention may be used as optical sensors. Optical sensors may comprise a long-lifetime fluorophore such as a ruthenium based α-diimine complex, e.g., tris(4,7-diphenyl-1,10-phenanthroline) ruthenium (II) salt (Ru(DPP)$_3^{2+}$) or tris-2,2'-bipyridyl ruthenium (II) salt. Other transition metal ligand complexes containing platinum or palladium complexed to, but not limited to, porphyrines may also be used. The optical sensors may be immobilized within, inter alia, a silicon film, polystyrene or cellulose acetate.

The present invention can be used to detect and/or to quantify a particular parameter in a sample. The fluorophores or optical sensors may detect, although not be limited to, analytes such as gaseous or dissolved oxygen. For example oxygen dynamically quenches fluorescence of sensors with lifetimes >20 ns. Both fluorescence lifetime and fluorescence intensity are decreased. The respective relationships are:

$$\tau_0/\tau = 1 + k_{sv}[O_2]$$

and $$L_0/L = 1 + k_{sv}[O_2]$$

where $\tau_0$ and $L_0$ are lifetime and intensity in the absence of oxygen, $\tau$ and $L$ are lifetime and intensity in the presence of oxygen and $K_{sv}$ is the Stern-Volmer coefficient. Because fluorescence lifetime is subject to many fewer variables than fluorescence intensity, it is preferable to measure it. It is also contemplated that other photochemical studies may be performed using the device and methods disclosed herein. For example, by varying the width of the gate and the frequency, the device may be used to detect the variations in the fluorescence lifetimes and fractional intensities of an optical sensor during dye photobleaching. Additionally, it is contemplated that alternate frequency domain methods to determine lifetime from gated data may be used.

As described herein, the invention provides a number of therapeutic advantages and uses. The embodiments and variations described in detail herein are to be interpreted by the appended claims and equivalents thereof. The following examples are given for the purpose of illustrating various embodiments of the invention and are not meant to limit the present invention in any fashion.

EXAMPLE 1

Gated Versus Ungated Detection

Figure 7A:
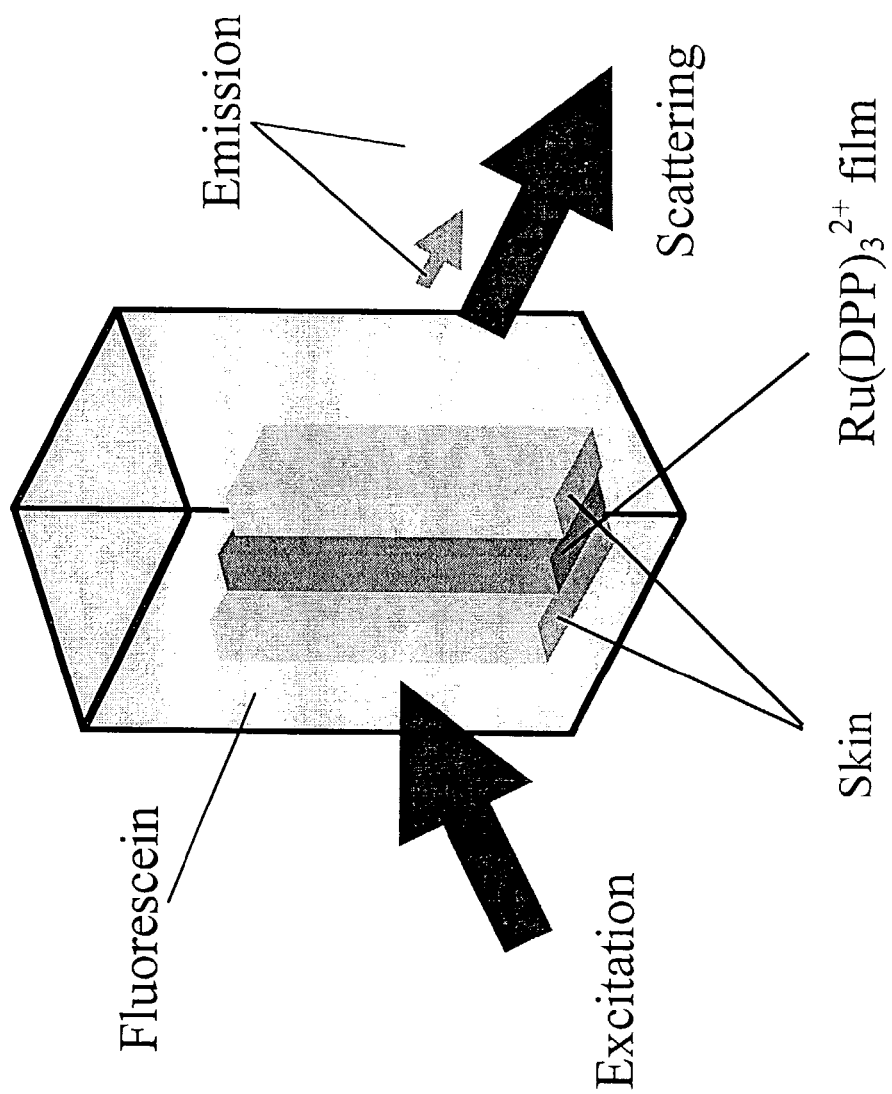
FIG. 7A pictorially represents the effect of no gating on detection of lifetime fluorescence of a fluorescent film in the presence of background and scattered emissions.
Figure 7B:
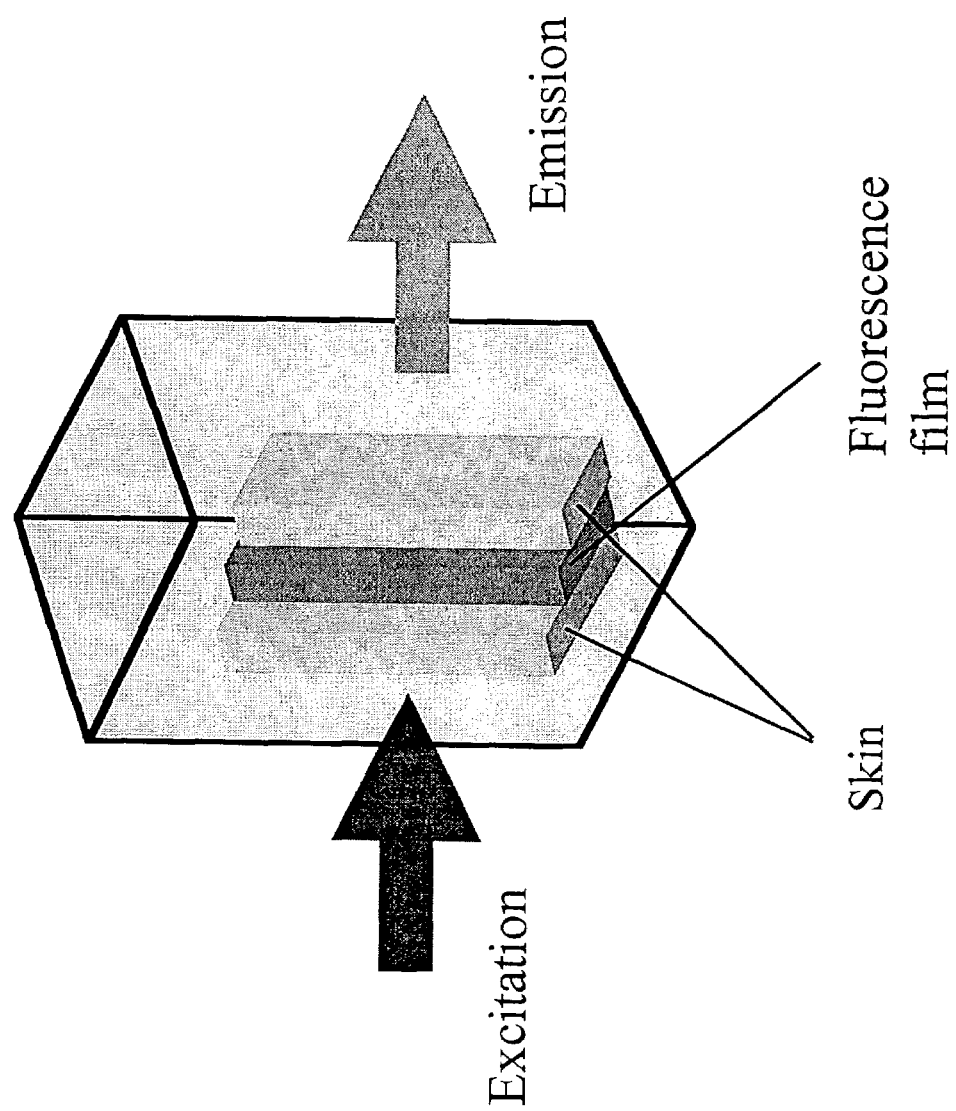
FIG. 7B pictorially represents the effect of gating on detection of lifetime fluorescence of a fluorescent film in the presence of background and scattered emissions.

The fluorescent signal from a sample consisting of a $(Ru(DPP)_3^{2+})$ doped film in a fluorescein solution is measured with no gating and with gating. Fluorescein is roughly three times brighter than the fluorophore and simulates the background. Skin is a highly scattering medium and is difficult to measure through. The ungated signal is the sum of scattered excitation, fluorescein and $Ru(DPP)_3^{2+}$ emissions and demonstrates that the emission from the optical sensor is overwhelmed by the background and scattered emissions (FIG. 7A) when compared to a gated signal which only shows the emission from the $Ru(DPP)_3^{2+}$ (FIG. 7B).

Figure 8B:
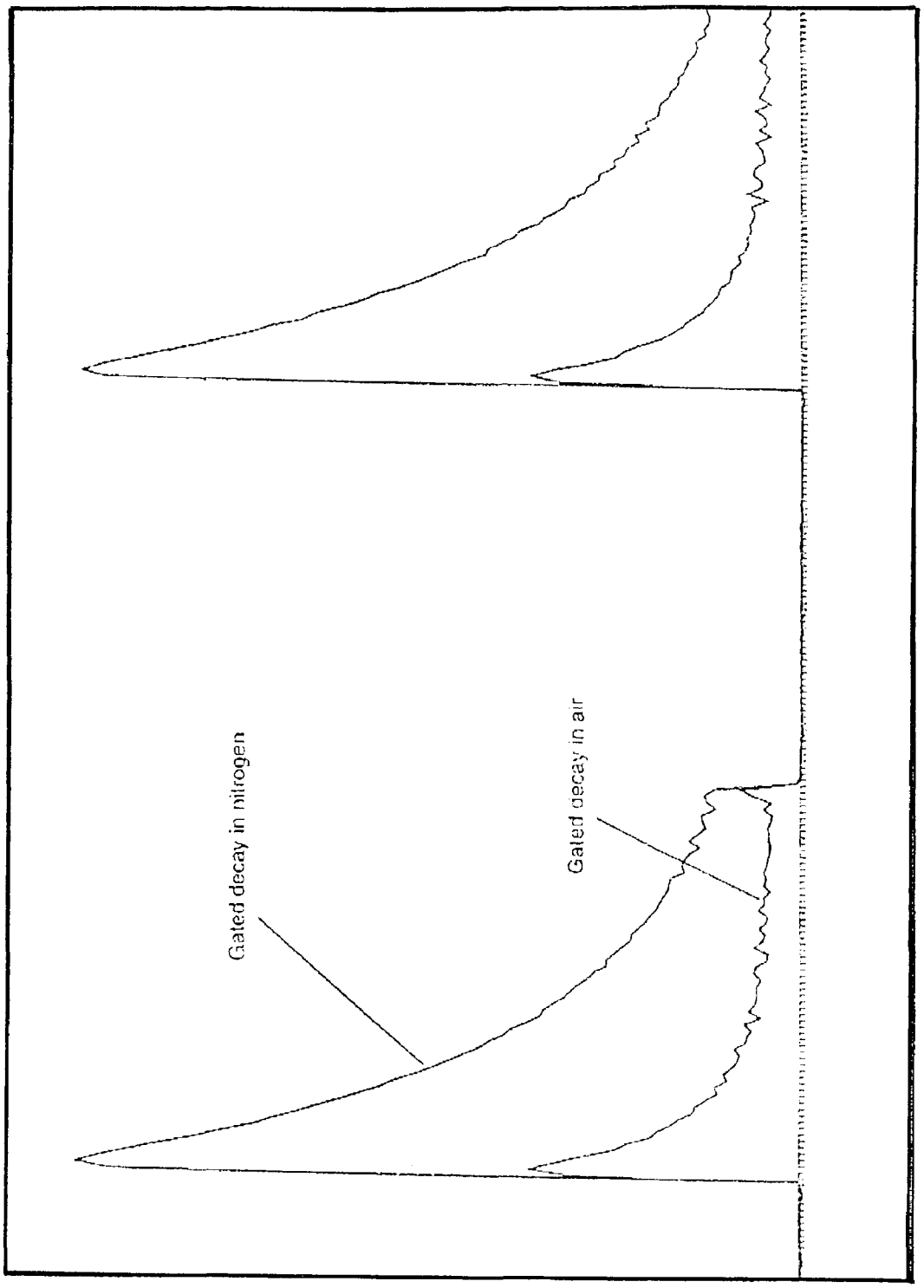
FIG. 8B compares the lifetime fluorescent decay of $Ru(dpp)_3^{2+}$ in a silicone film in the presence of nitrogen with that in the presence of air.
Figure 8A:
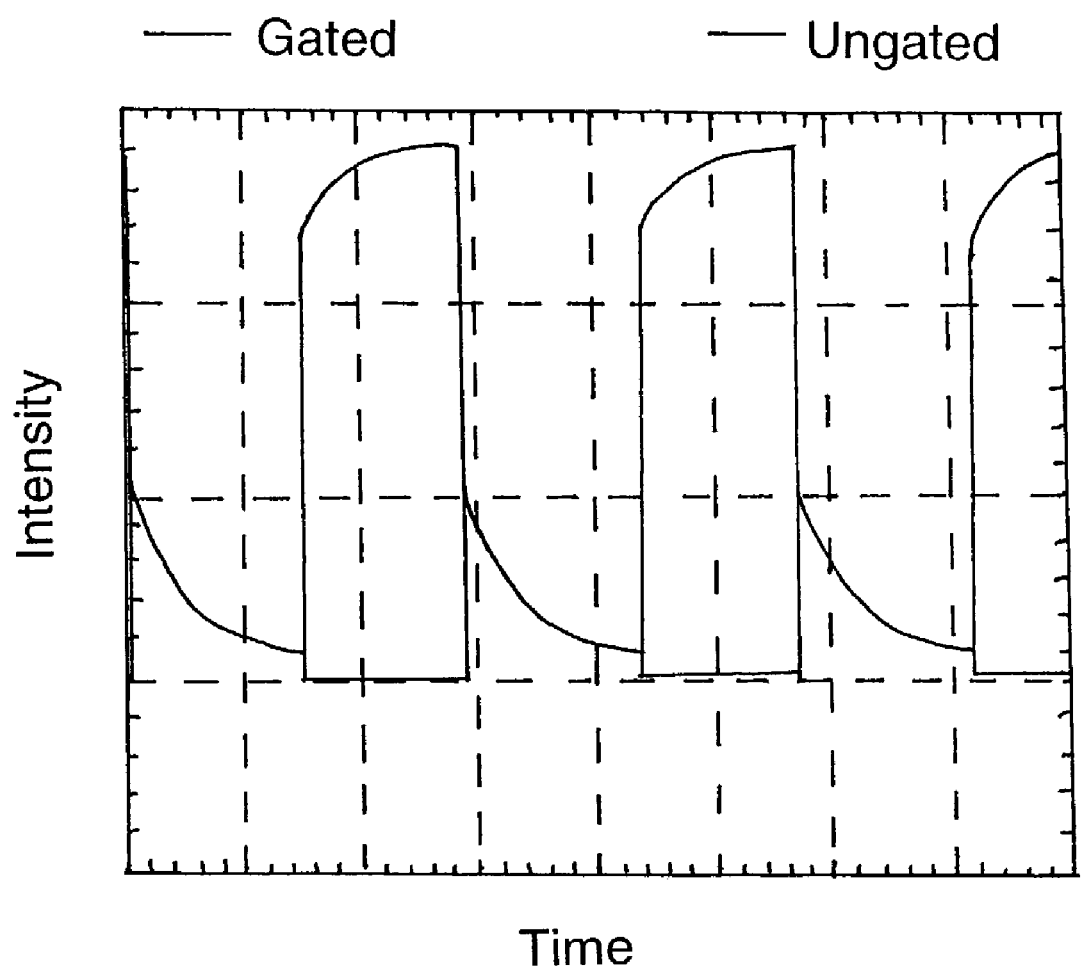
FIG. 8A compares the lifetime fluorescent decay of $Ru(dpp)_3^{2+}$ in fluorescein with and without gating the signal.

The gated and ungated signals overlap when the LED is off. When gating is applied, the photodetector does not "see" the strong background (FIG. 8A). FIG. 8B compares gated signals in air and nitrogen. The decay of the gated emission signal in air compared to that in nitrogen demonstrates that the $Ru(DPP)_3^{2+}$ is quenched by the oxygen in the air. These signals are digitized and all further mathematical operations performed by computer. The resulting phase shifts were obtained by using a sinusoidal mixing signal and demonstrate good correlation with phase shifts obtained under sinusoidal excitation in the absence of background fluorescence

EXAMPLE 2

Figure 9:
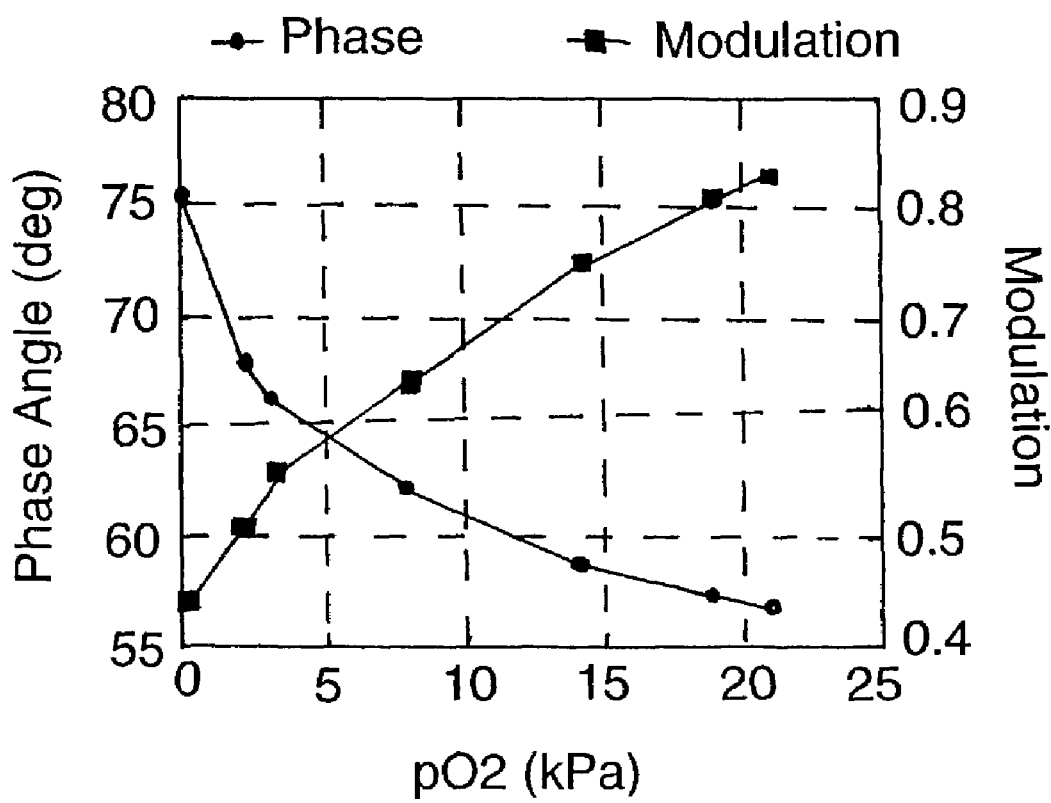
FIG. 9 compares both phase angle and modulation of the lifetime of $Ru(dpp)_3^{2+}$ in a silicon film in the presence of increasing partial pressures of oxygen.

Measurment of Oxygen Concentration using $Ru(DPP)_3^{2+}$ $Ru(DPP)_3^{2+}$ contained within a silicon film is placed in a fluorescein solution in a cuvette. The film is further wrapped in a layer of chicken skin. Thus, the set-up provides an environment with significant backscatter and autofluorescence. FIG. 9 demonstrates that as the partial pressure of oxygen increases, the phase angle decreases, i.e., the oxygen binds the ruthenium (II) in the complex thereby quenching fluorescence lifetime, and the modulation approaches 1. Although measurements were made in a highly scattering environment, gated detection easily removes the effect of scattered light due to the chicken skin.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for determining fluorescence lifetimes of a fluorophor comprising the steps of:
    exciting said fluorophor with light from a pulsed light source;
    gating a photodetector during excitation of said fluorophore;
    detecting light emitted from said fluorophor with said photodetector, said emission light exhibiting a phase shift in frequency from that of said excitation light; and
    converting said detected emitted light to an amplified electric signal; and
    evaluating said amplified electric signal as a measure of fluorescence lifetime of said fluorophor.

2. The method of claim 1, wherein the pulsed light source is a light emitting diode.

3. The method of claim 2, wherein said light emitting diode emits a wavelength of about 470 nm.

4. The method of claim 1, wherein said photodetector is gated via a variable gain amplifier.

5. The method of claim 1, wherein said photodetector is gated via a first switch and a second switch, wherein if one of said first or said second switches is on, the other of said first or said second switches is off.

6. The method of claim 5, wherein said photodetector is gated when said first gating switch is on and said second gating switch is off.

7. The method of claim 5, wherein when said second gating switch is on, said photodetector detects said emission signal.

8. The method of claim 1, wherein said photodetector is a photodiode.

9. The method of claim 1, wherein said gating step prevents detection of light other than said measured emission light.

10. The method of claim 9, wherein said other light is said excitation light, ambient light or short-lived light comprising scattered light or fluorescence having a time constant about 10 times smaller than the lifetime of said emission light from said fluorophor.

11. The method of claim 1, wherein said emission light is converted to an amplified electric signal via a transimpedance amplifier or a variable gain amplifier.

12. The method of claim 1, wherein said amplified electric signal is evaluated as fluorescence lifetime via a computer.

13. The method of claim 1, further comprising the step of correlating said fluorescence lifetime of said fluorophor to an analyte present in the immediate environment of said fluorophor or to a parameter of said immediate environment.

14. The method of claim 13, wherein said analyte is dissolved oxygen or gaseous oxygen.

15. The method of claim 1, wherein said fluorophor is used as an optical sensor.

16. The method of claim 15, wherein said optical sensor is a ruthenium-, a platinum- or a palladium-based ligand complex.

17. The method of claim 16, wherein said complex is tris(4,7-diphenyl-1,10-penanthroline) ruthenium (II) salt or tris-2,2'-bipyridyl ruthenium (II) salt.

18. A device for determining fluorescence lifetime of a fluorophor comprising:
    a means for delivering a pulsed excitation signal to said fluorophor, said excitation signal exciting said fluorophor to emit a fluorescent signal exhibiting a phase shift in frequency from that of said excitation signal;
    a means for detecting said emission signal emitted from said fluorophor;
    a means for gating said detection means during delivery of said excitation signal and prior to detection of said emission signal;
    a means for converting said detected emission signal to an amplified electrical signal; and
    a means for evaluating said amplified electrical signal as fluorescence lifetime of said fluorophor.

19. The device of claim 18, wherein said means for delivering said excitation signal comprises a light emitting diode and a driver thereof.

20. The device of claim 19, wherein said light emitting diode emits a wavelength of about 470 nm.

21. The device of claim 18, wherein said means of detecting said emission signal is a photodiode.

22. The device of claim 18, wherein said means for gating comprises a variable gain amplifier.

23. The device of claim 18, wherein said means for gating said detection means comprises a first switch and a second switch, wherein if one of said first or said second switches is on, the other of said first or said second switches is off.

24. The device of claim 23, wherein said detection means is gated when said first gating switch is on and said second gating switch is off.

25. The device of claim 23, wherein when said second gating switch is on, said detection means detects said emission signal.

26. The device of claim 18, wherein said means of converting said detected emission signal to an amplified electrical signal comprises a transimpedance amplifier or a variable gain amplifier.

27. The device of claim 18, wherein said means for evaluating said amplified electric signal comprises a computer having means to receive said amplified electric signal.

28. The device of claim 27, wherein said computer further comprises means for synchronizing interaction of all of said means.

29. The device of claim 28, wherein said means for synchronizing interaction of all of said means comprises an analog-to-digital converter/data conversion card (ADC/DAC).

30. The device of claim 27, wherein said computer further comprises means for correlating said fluorescence lifetime of said fluorophor to an analyte present in the immediate environment of said fluorophor or to a parameter of said immediate environment.

31. The device of claim 30, wherein said analyte is dissolved oxygen or gaseous oxygen.

32. The device of claim 18, wherein said fluorophor is used as an optical sensor.

33. The device of claim 32, wherein said optical sensor is a ruthenium-, a platinum- or a palladium-based ligand complex.

34. The device of claim 33, wherein said complex is tris(4,7-diphenyl-1,10-penanthroline) ruthenium (II) salt or tris-2,2'-bipyridyl ruthenium (II) salt.

* * * * *